United States Patent
Castor et al.

(10) Patent No.: US 6,745,771 B2
(45) Date of Patent: Jun. 8, 2004

(54) ANESTHETIC FILTER ARRANGEMENT WITH VARIABLE RETENTION OF GAS BY THE FILTER

(75) Inventors: Rolf Castor, Trangsund (SE); Petter Videbrink, Upplands Vasby (SE)

(73) Assignee: Siemens Elema AB, Solna (SE)

( * ) Notice: Subject to any disclaimer, the term of this patent is extended or adjusted under 35 U.S.C. 154(b) by 47 days.

(21) Appl. No.: 10/013,246

(22) Filed: Dec. 10, 2001

(65) Prior Publication Data

US 2002/0104542 A1 Aug. 8, 2002

(30) Foreign Application Priority Data

Jan. 10, 2001 (SE) ................................. 0100064

(51) Int. Cl.⁷ ............................................. A62B 23/02
(52) U.S. Cl. ............................... 128/205.27; 128/203.12
(58) Field of Search ....................... 128/203.12, 203.13, 128/203.14, 204.18, 204.21, 204.22, 204.23, 205.12–205.15, 204.14, 204.15, 204.16, 204.17, 205.28, 205, 27, 911, 912, 910; 55/486, 487, 490, 490.1, 512, DIG. 32; 95/900, 901, 902, 139; 96/108, 214, 126, 15

(56) References Cited

U.S. PATENT DOCUMENTS

| | | | |
|---|---|---|---|
| 3,183,906 A | | 5/1965 | Moyat |
| 5,044,361 A | | 9/1991 | Werner et al. |
| 5,110,569 A | * | 5/1992 | Jain ............................ 423/230 |
| 5,471,979 A | | 12/1995 | Psaros et al. |
| 5,507,280 A | * | 4/1996 | Henkin et al. ......... 128/203.12 |
| 5,515,845 A | * | 5/1996 | Filipovic et al. ....... 128/205.12 |
| 5,806,513 A | * | 9/1998 | Tham et al. ........... 128/204.22 |
| 6,095,137 A | * | 8/2000 | Wallroth et al. ....... 128/203.26 |
| 6,123,069 A | * | 9/2000 | Davis .................... 128/202.26 |
| 6,152,133 A | * | 11/2000 | Psaros et al. .......... 128/205.12 |
| 6,206,002 B1 | * | 3/2001 | Lambert ................ 128/205.12 |
| 6,279,576 B1 | * | 8/2001 | Lambert ................ 128/205.28 |
| 6,328,036 B1 | * | 12/2001 | Emtell et al. .......... 128/205.14 |
| 6,354,292 B1 | * | 3/2002 | Fisher ................... 128/203.12 |
| 6,405,539 B1 | * | 6/2002 | Stach et al. ................... 62/3.4 |
| 6,425,937 B1 | * | 7/2002 | Kraus et al. ................. 95/90 |
| 6,523,538 B1 | * | 2/2003 | Wikefeldt ............. 128/204.18 |
| 6,562,113 B1 | * | 5/2003 | Aykanian et al. ............. 96/143 |
| 6,632,269 B1 | * | 10/2003 | Najm .......................... 95/273 |
| 2001/0022181 A1 | * | 9/2001 | Masson et al. ........ 128/203.12 |

FOREIGN PATENT DOCUMENTS

| | | |
|---|---|---|
| DE | 30 00 191 | 7/1980 |
| DE | 195 49 271 | 7/1997 |
| EP | 0 284 227 | 9/1988 |
| FR | 1416169 | 9/1965 |

\* cited by examiner

*Primary Examiner*—Aaron J. Lewis
*Assistant Examiner*—Teena Mitchell
(74) *Attorney, Agent, or Firm*—Schiff Hardin & Waite

(57) ABSTRACT

An anesthetic filter arrangement has a filter housing with openings disposed to delimit a gas flow path inside the housing for gas passing to and from a patient, and having disposed within the gas flow path a filter element formed of an adsorption material for the alternate adsorption and desorption of gaseous anesthetic from and into gas passing along the gas flow path respectively from and to the patient. An energy source is provided to supply thermal and/or vibrational energy at the filter element to vary retention of the gaseous anesthetic by the filter element.

9 Claims, 3 Drawing Sheets

ANESTHETIC FILTER ARRANGEMENT WITH VARIABLE RETENTION OF GAS BY THE FILTER

BACKGROUND OF THE INVENTION

1. Field of the Invention

The present invention relates to an anesthetic filter arrangement and in particular to a filter arrangement for the re-use of anesthetics in inhalation anaesthesia.

2. Description of the Prior Art

Filter arrangements for the re-use of gaseous anesthetics are well known and are described in, for example U.S. Pat. Nos. 5,044,361 and 5,471,979. These filter arrangements generally have a filter housing in which there are provided openings delimiting a gas flow path through the interior of the housing. Disposed within the gas flow path is a filter element of an adsorption material for the alternate adsorption and desorption of gaseous anesthetic from and into gas passing along the flow path. These filters are placed within gas flow circuits of anesthetic ventilator systems so that anesthetic rich gas which is exhaled by a patient into the gas flow circuit during an expiration phase passes through the filter element along the flow path in one flow direction and so that breathing gas in the gas flow circuit which is to be supplied to the patient during an inspiration phase passes through the filter element along the flow path, usually but not necessarily, in the opposite flow direction. The filter element adsorbs gaseous anesthetic from the exhaled gas then desorbs this adsorbed gaseous anesthetic into the breathing gas.

Such filter arrangements suffer from the disadvantage that their retention properties for the gaseous anesthetic are fixed, dependent on the adsorption and desorption characteristics of the filter element material. Adsorption and desorption of gaseous anesthetic to and from the filter element is then largely controlled by varying the flow of and to a lesser extent the concentration of gaseous anesthetic in gas passing along the gas flow path, through the filter element. However, varying the gas flow and concentration parameters may have undesirable effects on the ventilation of a patient who is connected to an anesthetic ventilator system in which the filter arrangement is disposed.

SUMMARY OF THE INVENTION

It is an object of the present invention to provide an anesthetic filter arrangement, as well as an inhalation anesthetic system employing such a filter, wherein the degree of retention of gaseous anesthetic by a filter element can be varied.

The above object is achieved in an embodiment of the present invention directed to an anesthetic filter arrangement wherein a filter housing has openings disposed to delimit a gas flow path in the interior of the housing adapted for passing gas to and from a patient, wherein a filter element, formed of an adsorption material is disposed in the gas flow path for alternatingly adsorbing gaseous anesthetic from and desorbing gaseous anesthetic into gas in the gas flow path, and wherein an energy source is in energy transferring communication with the filter element for supplying energy to the filter element to vary the retention of the gaseous anesthetic by the filter element.

The retention of gaseous anesthetic by the filter element is thus varied through supplying either thermal or vibrational energy, at the element which thereby varies the adsorption and/or desorption of gaseous anesthetic.

The thermal energy may be supplied to the filter element using an energy source formed by a resistive heater element, for example a thin wire, which can be placed in intimate thermal contact with the filter element, for example within the volume of the element material.

Alternatively, the material of the filter element may be electrically conducting, for example activated carbon material, and used as the resistive heater element. This has the advantage that the thermal energy can be evenly distributed throughout the entire volume of the filter element without the need for integrating a separate resistive heater element.

An electromagnetic energy source, such as an infra-red or microwave source may be employed to supply the thermal energy at the element. This has an advantage that the source may be located remote from the filter element which permits the use of a disposable filter element without the need to also dispose of components of the energy source.

A source of vibrational energy, such as an acoustic, preferably ultrasonic, vibrational energy source, may be employed as the energy source. This has the advantage that the vibrational energy can be supplied from outside the filter housing, for example by using vibrational sources detachably mounted to an external surface of the housing. This permits the re-use of the vibrational sources when used with disposable filter elements and housings and also the ready modification of existing filter housings.

The above object is also achieved in accordance with the principles of the present invention in an embodiment directed to an inhalation anesthetic system having a mechanical breathing aid for supplying a breathing gas, including an anesthetic gas, to ventilate a patient, a gas circuit connected to the breathing aid for conducting the breathing gas to the patient during an inspiration phase and for conducting exhaled gas from the patient during an expiration phase, and an anesthetic filter arrangement as described above disposed in the gas circuit, with the aforementioned alternating absorption and desorption of the gaseous anesthetic taking place in the expiration phase and the inspiration phase, respectively.

DESCRIPTION OF THE PREFERRED EMBODIMENTS

Figure 1:
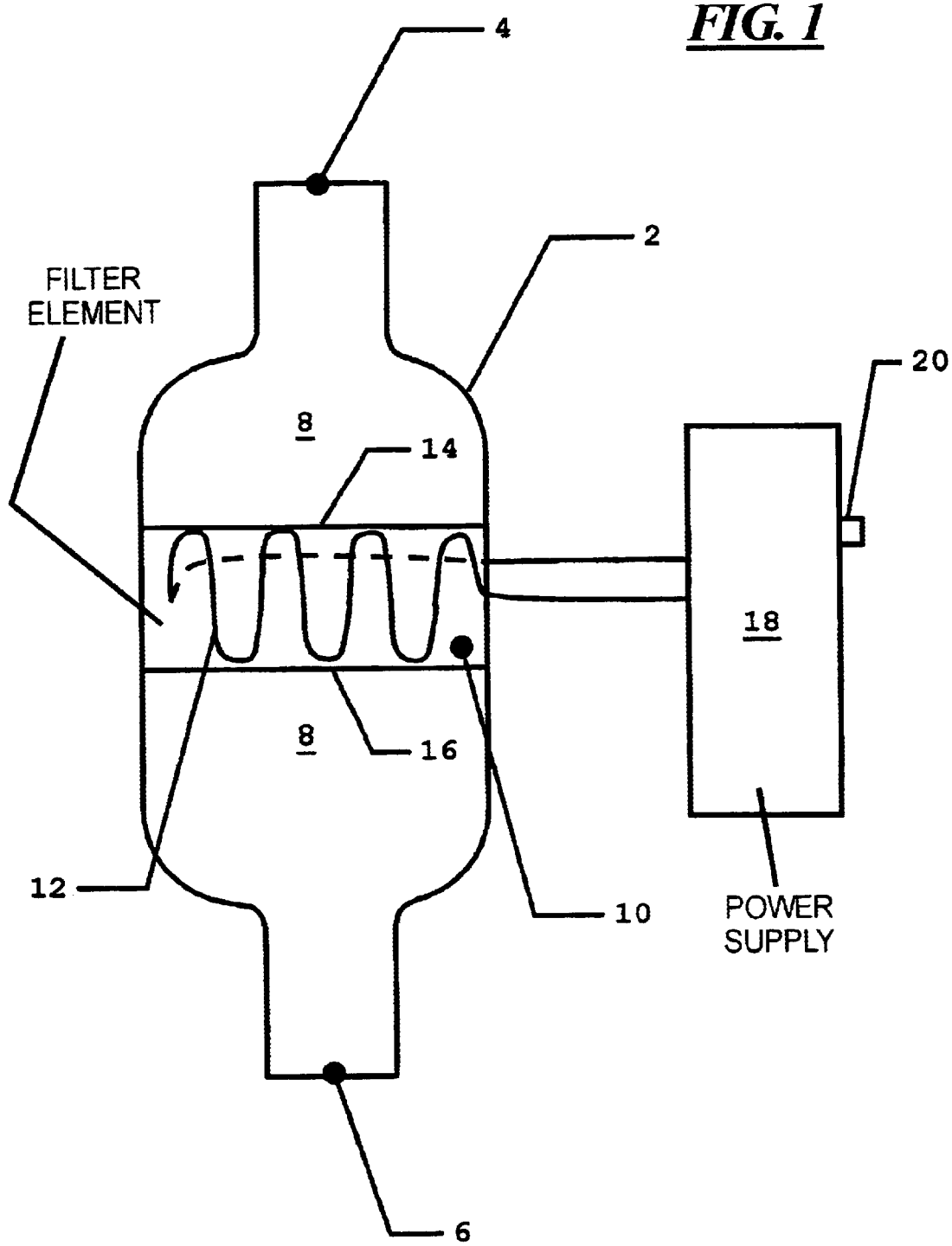
FIG. 1 shows an embodiment of a filter arrangement according to the present invention.

As shown in FIG. 1, an anesthetic filter arrangement is shown comprising a filter housing 2 having openings 4,6 for leading a gas to and from the interior 8 of the housing 2. Contained within the interior 8 of the housing 2 in a gas flow path delimited by the openings 4,6 is a filter element 10 formed of a suitable adsorption material such as zeolites of crystalline aluminum silicates which may be pellets or supported on a carrier; or an activated carbon filter such as formed from carbon-impregnated material, carbon fiber cloth, or granulated or microporous carbon material.

A resistive heater element 12 formed by a thin electrical conductor is, in the present embodiment, provided within the volume of the filter element 10. This heater element 12 alternatively may be disposed across one or both outer surfaces 14,16 of the filter element 10 and may even be utilized as a carrier for the adsorption material from which the element 10 is formed provided that passage of gas through the filter element 10 is not significantly inhibited. If an activated charcoal material is used in the filter element 10 then the carbon material itself can be used as the resistive heater element and the separate element 12 is not required.

A supply 18 is also provided to energize the heater element 12 (or the filter element material directly) to supply thermal energy for weakening any bond between adsorbed gaseous anesthetic and the material of the filter element 10. In this manner desorption may be promoted or adsorption inhibited, dependent on when the energy is supplied. This power supply is here provided with an interface 20 for receiving control signals which are employed to vary one or both of the level and the duration of the power supplied to the heater element 12 from the supply 18. It will be appreciated that the nature of this control signal is largely a design choice and may be produced for example by a flow meter located in a gas flow path outside but connected to the openings 4,6 of the housing 2 and may be used to synchronize the supply of power with a gas flow, as will be described in greater detail below. Other control modes (not shown) for example internal timing circuitry or simply a manual control such as a manually variable resistor or an on/off switch may be additionally or alternatively used to vary the level and/or duration of power supplied by the supply 18.

Figure 2:
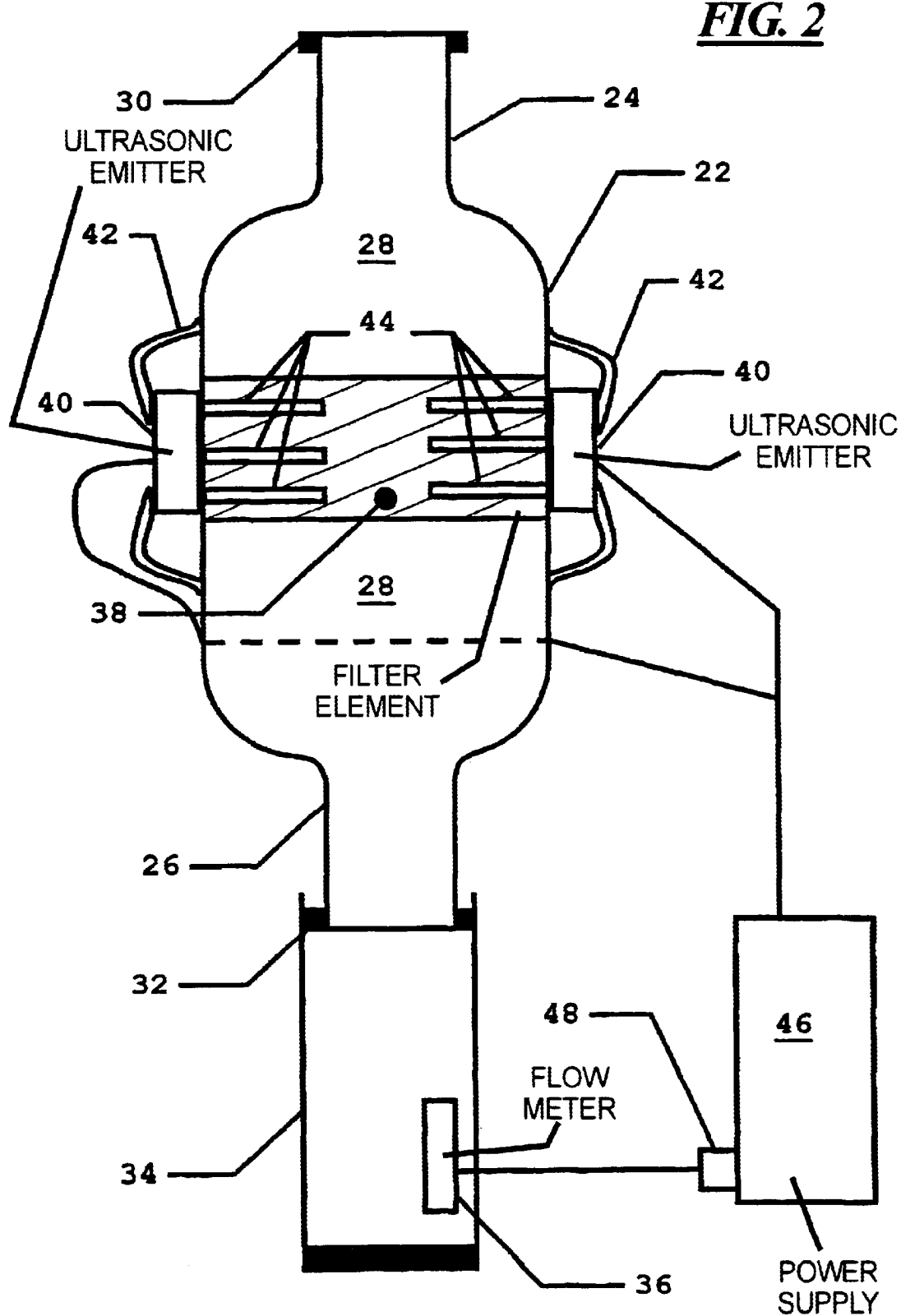
FIG. 2 shows a further embodiment of a filter arrangement according to the present invention.

Considering now the arrangement of FIG. 2, a filter housing 22 in which is provided openings 24,26 for leading a gas to and from the interior 28 of the housing 22 is shown. Sealing rings 30,32 are provided towards the ends of the openings 24,26, distal the interior 28 of the housing 22. These rings 30,32 are intended to form a releasable gas tight seal with a push fit conduit 34 inside which is contained a flow meter 36. The conduit 34 is shown in this example to be connected to the opening 26 of the housing but could be connected to the opposing opening 24.

Contained within the interior 28 of the housing 22 is a filter element 38 formed of a suitable adsorption material which may or may not be the material used in the arrangement of FIG. 1.

A pair of conventional ultrasonic emitters 40, such as are formed from piezoelectric discs, are releasably located facing one another in intimate contact to the outside of the housing 22 using retainings 42 so as to be able to direct ultrasonic waves into the interior 28 of the housing 22, toward the filter element 38. Preferably, the emitters 40 are positioned to overlay the volume of the housing 22 which, in use, contains the filter element 38. Optionally, thin vibratable rods 44 may be employed, as in the present embodiment, to enhance the transfer of vibrational energy from the emitters 40 into the bulk of the filter element 38. These rods 44 are preferably dimensioned to have a resonant frequency at or close to the frequency of ultrasound generated by the emitters 40.

A power supply 46 is connected to energize the emitters 40 and is provided with an interface 48 for receiving control signals from the flow meter 36. These signals are employed by the power supply 46 to vary the power supplied to the emitters 40,42. The flow meter 36 preferably provides a control signal to the interface 48 which is indicative of the direction of gas flow in the conduit 34 and the power supply 46 is adapted to respond to the control signal by starting or stopping the supply of power to the emitters 40 dependent on the flow direction. It will be appreciated from the following description of the use of the filter arrangement according to the present invention in the inhalation anesthetic system of FIG. 3 that the flow meter 36 may be substituted for a flow meter commonly found is such systems and used to control a breathing gas supply.

Figure 3:
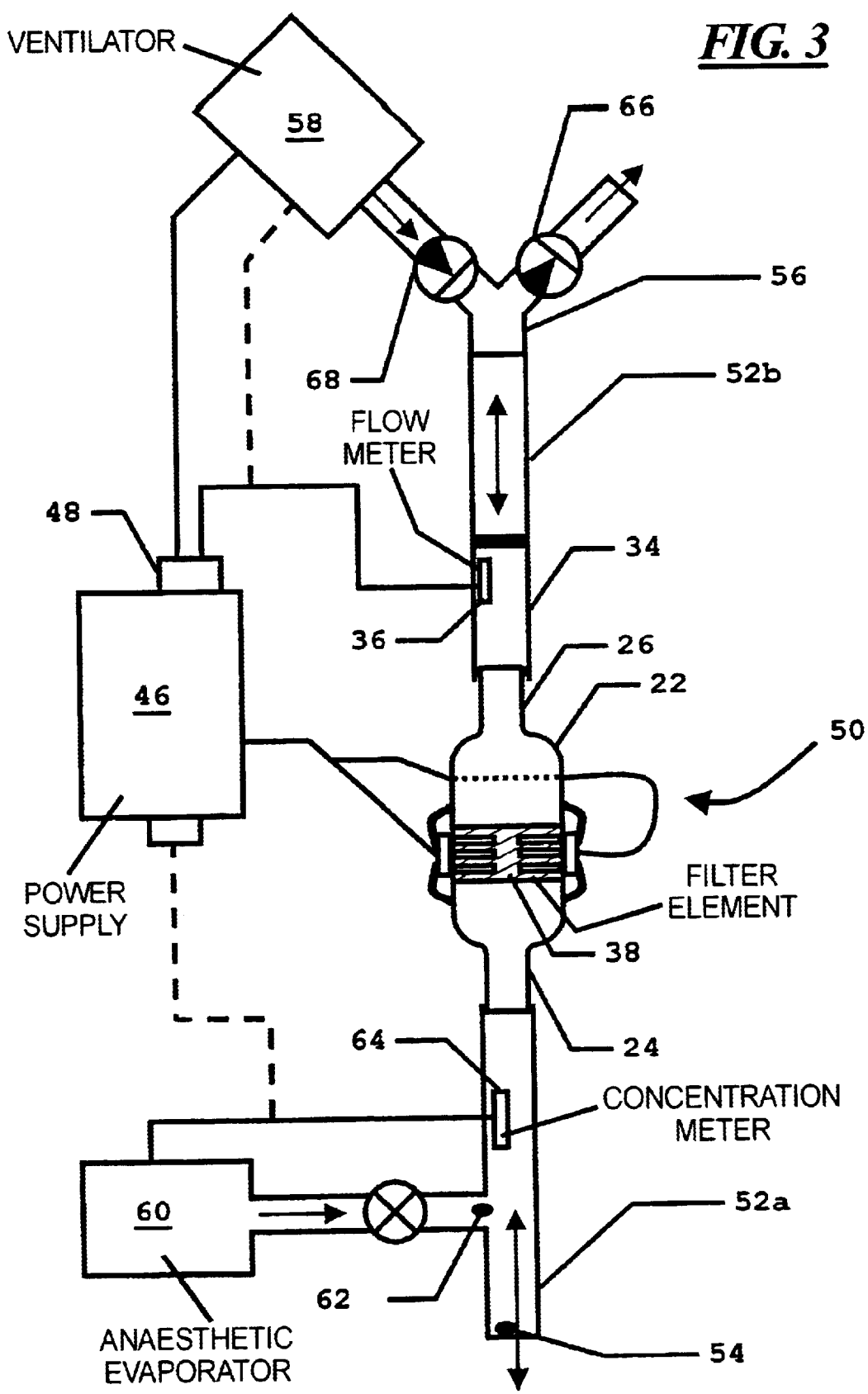
FIG. 3 shows an inhalation anesthetic system including as an element thereof a filter arrangement according to the present invention.

Considering now the anesthetic inhalation system of FIG. 3. An anesthetic filter arrangement 50 according to the present invention, being in the embodiment shown in FIG. 2, is disposed with the openings 24,26 connected in-line in a gas conduit 52a,b which has a section 52a having an open end 54 for connection to the airways of a patient (not shown) and a section 52b which connects via a 'Y-Piece' 56 to a conventional mechanical breathing device 58, in this example a mechanical ventilator, which is used to provide a breathing gas to the patient. The section 52b also connects via the Y-Piece 56 to atmosphere or to a gas collection system (not shown). The latter typically via a dedicated gas flow conduit in the ventilator 58. A conventional anesthetic evaporator 60 is connected to the section of gas conduit 52a via an outlet 62 located between the open end 54 of the conduit 52a and the filter housing 22 of the filter arrangement 50. The output of the evaporator is, in the present embodiment, controlled dependent on a desired anesthetic concentration, for example provided to the evaporator by a user, and a concentration of anesthetic in a breathing gas flowing in the conduit 52a, toward the patient. This latter concentration is conveniently monitored by a conventional concentration meter 64 which is preferably located between the outlet 62 and the filter housing 22 to monitor the concentration of anesthetic already in the breathing gas after passage through the filter element 38 of the filter arrangement 50.

In use anesthetic rich gas is exhaled by the patient during an expiration phase into the conduit 52a where it flows via the opening 24 of the filter housing 22 through the filter element 38 which adsorbs gaseous anesthetic from the gas. The gas then continues to flow along a flow path within the housing 22 and opens into the gas conduit 52b via the opening 26. At the Y-Piece 56 a one-way valve 66 prevents the exhaled gas from flowing towards the ventilator 58 and the gas passes through a second one-way valve 68 to atmosphere (or to a gas collection system if present).

It will be appreciated by those skilled in the art that the known ventilator 58 includes flow control valves as part of the breathing circuit within the ventilator which operate to regulate the supply of breathing gas and which are closed during the expiration phase so that the one-way valve 66 may be omitted. Indeed, similar flow control valves are often used to regulate the flow of exhaled gas if it passes through a gas flow path within the ventilator 58 and are closed during the supply of the breathing gas so that the one-way valve 68 may, in this circumstance, also be omitted.

In the present embodiment, the ventilator 58 operates during an inspiration phase to supply breathing gas via the one-way valve 66 and the Y-Piece 56 into the gas conduit 52b. The breathing gas then flows via the opening 26 through the filter element 38 where previously adsorbed gaseous anesthetic is desorbed into the breathing gas. The breathing gas flows out of the filter housing 22 via the opening 24 and into the gas conduit 52a where the anesthetic meter 64 measures the concentration of anesthetic and provides an indication of the same to the anesthetic evaporator 60 which uses the information to control the supply of anesthetic to the outlet 62 in order to achieve a desired anesthetic concentration in the breathing gas at the open end 54 of the gas conduit 52a.

As the breathing gas flows in the conduit 52b towards the opening 26 of the filter housing 22 it flows through the conduit 34 where the flow meter 36 registers at least the direction of flow and may also measure the magnitude of flow. These flow parameters can also be provided to the ventilator 58 (broken line connection in FIG. 3) where they may be employed to regulate the supply of breathing gas. Usually, in known inhalation anesthetic systems, a flow meter is provided to at least monitor the supply of breathing gas from the ventilator 58. It will be appreciated by those skilled in the art that the flow meter 36 of the filter arrangement 50 may be substituted for the flow meter of the anesthetic system, if provided. The advantage of providing a separate flow meter 36, as illustrated in the present embodiment, is that the filter arrangement 50 may be provided as a "stand-alone" device, operable independent of any anesthetic system in which it is connected.

A control signal indicating at least the direction of flow is passed from the flow meter 36 to the interface 48 of the power supply 46. The power supply 46 is adapted to energize the ultrasound emitters 40 of the filter arrangement 50 when the control signal indicates a flow of breathing gas from the ventilator 58, towards the filter housing 22. In addition the level of power supplied by the supply 46 to the emitters 40 may be varied dependent on the magnitude of the flow, as measured by the flow meter 36. The ultrasound energy emitted by the emitters 40 causes the filter element 38 and any adsorbed gaseous anesthetic to vibrate and thus promotes the desorption of the gaseous anesthetic into the breathing gas as it flows through the filter element 38. The operation of the energy supply 46 may also be made dependent on the output from the concentration meter 64 (broken line connection in FIG. 3) such that, for example, the level of energy supplied to the emitters 40 is reduced as the measured concentration approaches the desired value.

In order to achieve a greater uptake of anesthetic by the patient it is advantageous to desorb a greater amount of the adsorbed gaseous anesthetic in to the breathing gas at the commencement of its supply to the patient so that the anesthetic gas can reach deep into the lungs. The power supply 46 is in the present embodiment therefore adapted to generate and supply a greater amount of power at the commencement of the inspiration phase, as detected by the flow meter 36.

When attempting to revive the patient from the anesthetic narcosis it is a disadvantage to have gaseous anesthetic present on the filter element 38 through which the breathing gas will pass as it is supplied to the patient. Usefully then, the power supply 46 is adapted to energize the emitters 40 in response to a flow signal from the flow meter 36 which indicates gas flow during an expiration phase at the end of an anesthetic treatment. A signal indicating that it is the end of the anesthetic treatment may be provided by the ventilator 58 in response to a user input indicating the same. To this end the ventilator 58 is adapted to be operably connectable with the power supply 46. Alternatively the user input may be made in a conventional manner directly on the power supply 46 via a user interface such as a computer keyboard or a dedicated keypad(not shown). The vibrational energy supplied to the filter element 38 from the ultrasound emitters 40 during the expiration phase inhibits adsorption of gaseous anesthetic from exhaled gas so that little or no gaseous anesthetic can be desorbed from the filter element 38 into breathing gas in a subsequent inspiration phase.

It will be appreciated by those skilled in the art that whilst the filter arrangement according to the present invention is described, in relation to FIG. 3 above, in operable connection with an "open" inhalation anesthetic system the filter arrangement may also be employed in "closed" or "partially closed" circle re-breathing inhalation anesthetic systems, which are common in the art.

It will also be appreciated by those skilled in the art that the described embodiments of the present invention may be modified whilst remaining within the scope of the invention as claimed. For example, a vibrational and thermal energy source may be used in combination; or the number of ultrasound emitters may be varied and even a single emitter may be employed and/or the vibratable rods may be omitted.

Although modifications and changes may be suggested by those skilled in the art, it is the intention of the inventor to embody within the patent warranted hereon all changes and modifications as reasonably and properly come within the scope of his contribution to the art.

We claim as our invention:

1. An anesthetic filter arrangement comprising:

a filter housing having openings therein disposed to delimit a gas flow path in an interior of the housing adapted to receive gas, including a gaseous anesthetic, having a variable gas flow with a first phase wherein the gas is adapted to flow in said gas flow path in a direction toward a patient, and with a second phase wherein the gas is adapted to flow in said gas flow path in a direction away from a patient;

a filter element disposed in said gas flow path in said housing, said filter element being comprised of an adsorption material for said gaseous anesthetic; and an energy source in energy transferring communication with said filter element for supplying energy to said filter element, synchronized with at least one of said first and second phases, to vary retention of said gaseous anesthetic by said filter element by promoting desorption of said gaseous anesthetic in said first phase and inhibiting absorption of said gaseous anesthetic in said second phase.

2. A filter arrangement as claimed in claim 1 wherein said energy source supplies energy to said filter element to vary a temperature of said filter element to vary said retention of the gaseous anesthetic by the filter element.

3. A filter arrangement as claimed in claim 2 wherein said energy source comprises an electrical resistive heater disposed in thermal contact with said filter element.

4. A filter arrangement as claimed in claim 2 wherein said adsorption material is electrically conductive, and wherein said energy source comprises an electric power supply which supplies electric power to said adsorption material.

5. A filter arrangement as claimed in claim 1 wherein said energy source supplies vibrational energy to said filter element to vary said retention of the gaseous anesthetic by the filter element.

6. A filter arrangement as claimed in claim 5 wherein said energy source is an ultrasound emitter which directs ultrasonic vibrational energy toward said filter element.

7. A filter arrangement as claimed in claim 1 further comprising a flow meter disposed in said gas flow path for monitoring said gas flow, said flow meter being operably connected to said energy source and supplying an output signal to said energy source indicative of said gas flow, and wherein said energy source varies the supply of energy to said filter element dependent on said output from said flow meter.

8. A filter arrangement as claimed in claim 1 wherein said energy source is controlled to supply energy to said filter element at a commencement of said first phase of said gas flow.

9. An inhalation anesthesia system comprising:

a mechanical breathing aid for supplying a breathing gas, including an anesthetic gas, adapted to ventilate a patient in an inspiration phase and an expiration phase;

a gas circuit connected to the breathing aid and adapted for connection to a patient for conducting said breathing gas to a patient during said inspiration phase and for conducting exhaled gas from a patient during said expiration phase;

a filter housing connected in said gas circuit, said filter housing having openings therein which delimit a gas flow path through said housing for said breathing gas;

a filter element disposed in said gas flow path in said housing, said filter element being comprised of absorption material for said gaseous anesthetic; and an energy source in energy transferring communication with said filter element for supplying energy to said filter element, synchronized with at least one of said inspiration phase and said expiration phase, for varying retention of said gaseous anesthetic by said filter element by promoting desorption of said gaseous anesthetic in said inspiration phase and inhibiting absorption of said gaseous anesthetic in said expiration phase.

* * * * *